(12) United States Patent
Waizenegger et al.

(10) Patent No.: US 10,022,169 B2
(45) Date of Patent: Jul. 17, 2018

(54) CLOSING MEMBER FOR STERNAL CLOSURE, STERNAL CLOSURE SYSTEM COMPRISING SUCH CLOSING MEMBER AND STERNAL CLOSURE

(71) Applicant: Karl Leibinger Medizintechnik GmbH & Co. KG, Donau (DE)

(72) Inventors: Axel Waizenegger, Muehlheim (DE); Thomas Koett, Kolbingen (DE)

(73) Assignee: Karl Leibinger Medizintechnik GmbH & Co. KG, Donau (DE)

(*) Notice: Subject to any disclaimer, the term of this patent is extended or adjusted under 35 U.S.C. 154(b) by 786 days.

(21) Appl. No.: 14/486,854

(22) Filed: Sep. 15, 2014

(65) Prior Publication Data

US 2015/0080895 A1    Mar. 19, 2015

(30) Foreign Application Priority Data

Sep. 18, 2013 (EP) .................................... 13184978

(51) Int. Cl.
*A61B 17/80* (2006.01)
*A61B 90/00* (2016.01)

(52) U.S. Cl.
CPC ........ *A61B 17/8076* (2013.01); *A61B 17/809* (2013.01); *A61B 17/8085* (2013.01); *A61B 2090/037* (2016.02); *F04C 2270/0421* (2013.01)

(58) Field of Classification Search
CPC ............ A61B 17/8076; A61B 17/8023; A61B 17/8004
See application file for complete search history.

(56) References Cited

U.S. PATENT DOCUMENTS 5,380,324 A * 1/1995 Muller ............... A61B 17/7002
606/256
7,803,176 B2 * 9/2010 Teague ............... A61B 17/8076
24/309
(Continued)

FOREIGN PATENT DOCUMENTS

DE    87 03 432    5/1987
DE    602 08 880   11/2006
(Continued)

OTHER PUBLICATIONS

European Search Report dated Feb. 18, 2013 from European Application No. 12184854.3.
(Continued)

*Primary Examiner* — Andrew Yang
(74) *Attorney, Agent, or Firm* — Beyer Law Group LLP

(57) ABSTRACT

The invention relates to a closing member for a sternal closure which is adapted to be mounted on a human or animal body in the region of the sternum for closing a cleft therein, wherein the closing member includes a first rear engaging area and a second rear engaging area, wherein, on the one hand, the first rear engaging area is prepared for positive securing on a first mounting area of the sternal closure on the one side of the cleft and, on the other hand, the second rear engaging area is prepared for positive securing on a second mounting area of the sternal closure on the other side of the cleft; to a sternal closure system comprising two first and second securing portions spaced apart from each other and adapted to be mounted on the human or animal body on both sides of a cleft in the region of a sternum as well as such closing member; and to a sternal closure.

10 Claims, 11 Drawing Sheets

(56) References Cited

U.S. PATENT DOCUMENTS

Figures 1, 2, 3, 4:
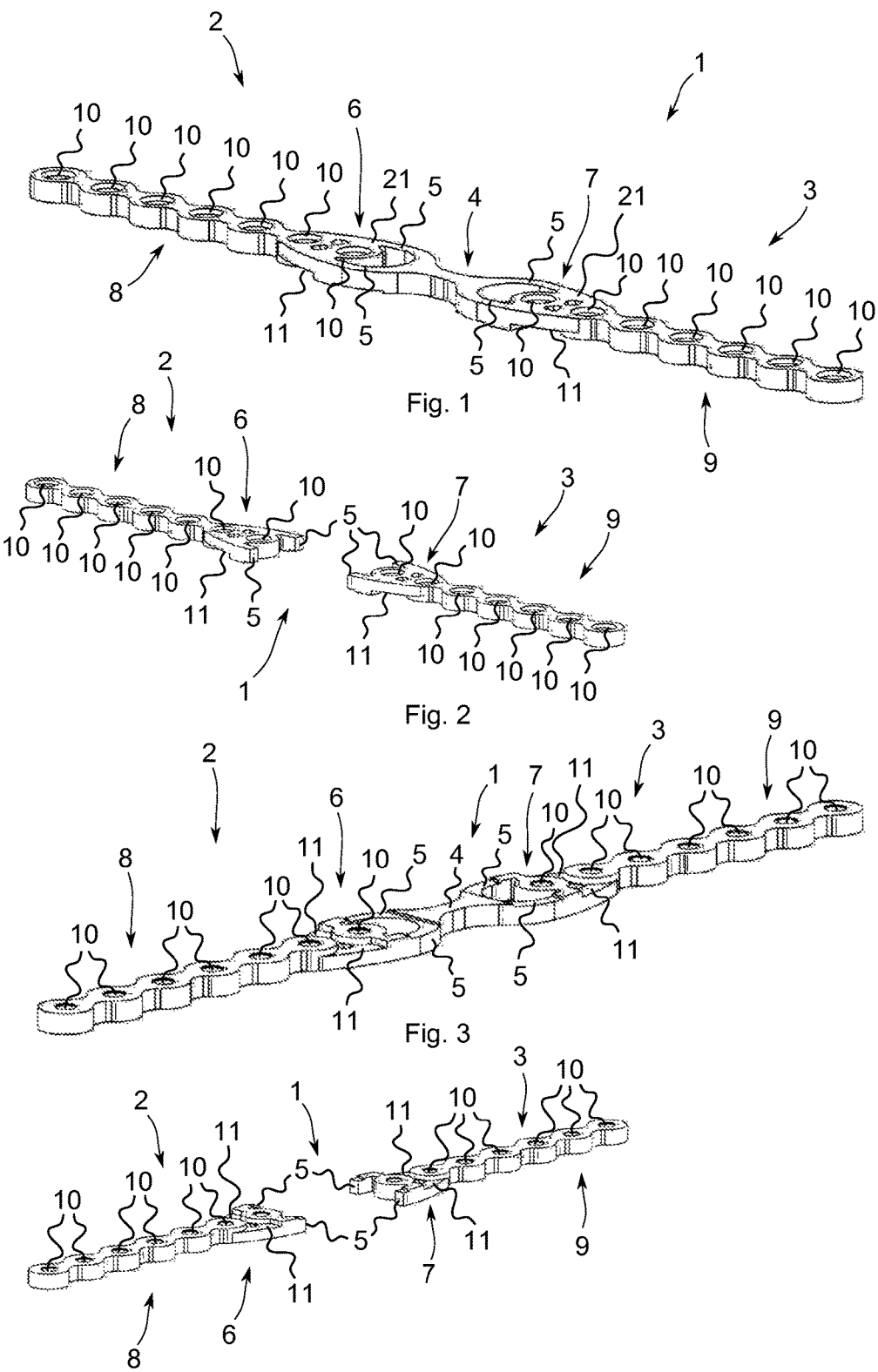

| | | | |
|---|---|---|---|
| 2002/0128654 A1 | 9/2002 | Steger et al. | |
| 2005/0065521 A1* | 3/2005 | Steger | A61B 17/80 606/281 |
| 2006/0015103 A1 | 1/2006 | Burke | |
| 2007/0038218 A1 | 2/2007 | Grevious | |
| 2011/0125193 A1 | 5/2011 | Grevious | |
| 2011/0313474 A1* | 12/2011 | Gabele | A61B 17/8004 606/324 |
| 2013/0018425 A1 | 1/2013 | Seldin et al. | |

FOREIGN PATENT DOCUMENTS

| | | |
|---|---|---|
| DE | 20 2010 012 426 | 11/2010 |
| EP | 1 654 994 | 5/2006 |
| WO | WO 03/061493 | 7/2003 |
| WO | 2008/073898 | 6/2008 |
| WO | WO 2008/073898 | 6/2008 |
| WO | WO 2012/162733 | 12/2012 |

OTHER PUBLICATIONS

European Search Report dated Oct. 15, 2013 from European Application No. 13184978.8.
U.S. Appl. No. 14/029,430, filed Sep. 17, 2013.

\* cited by examiner

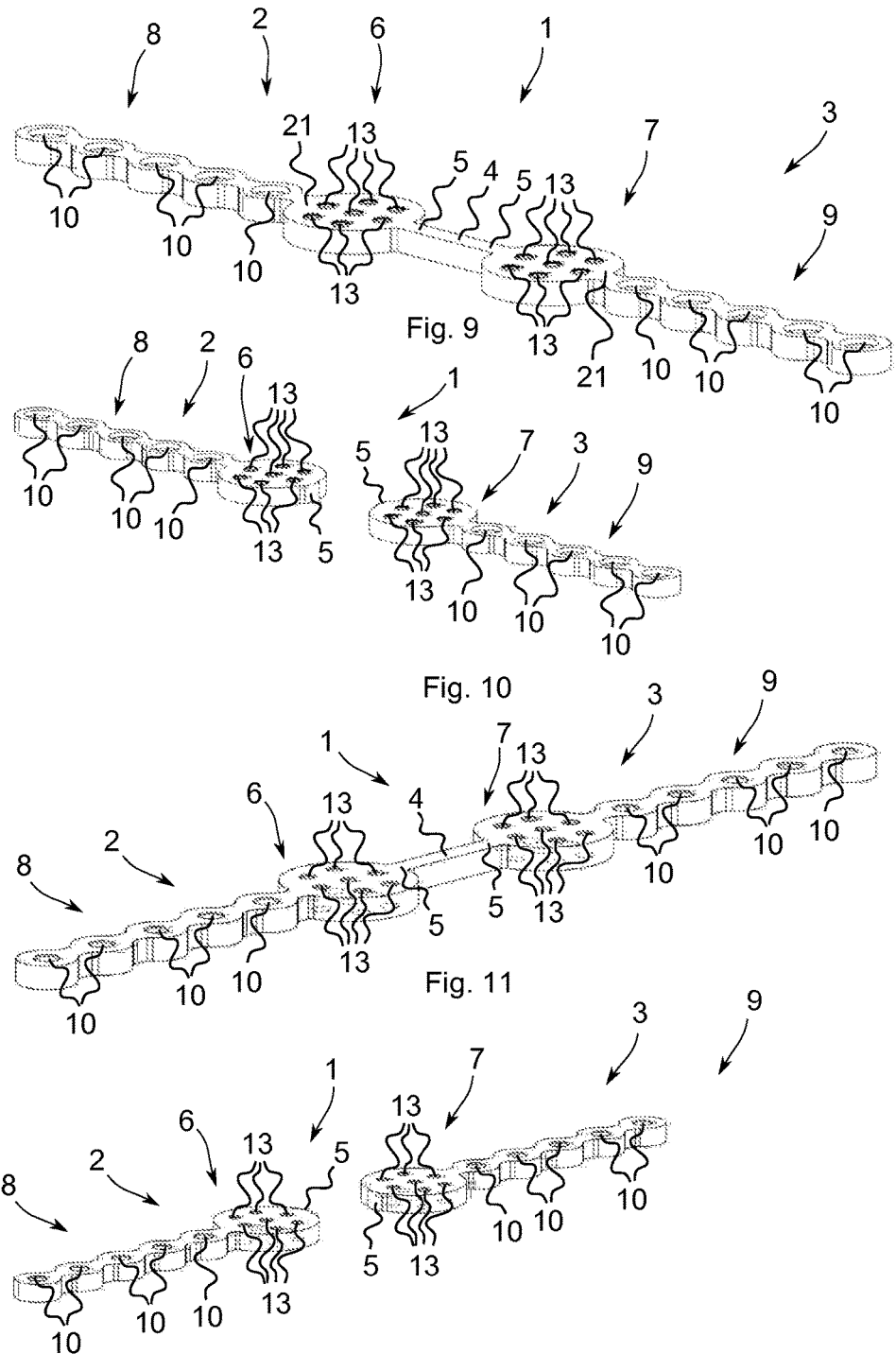

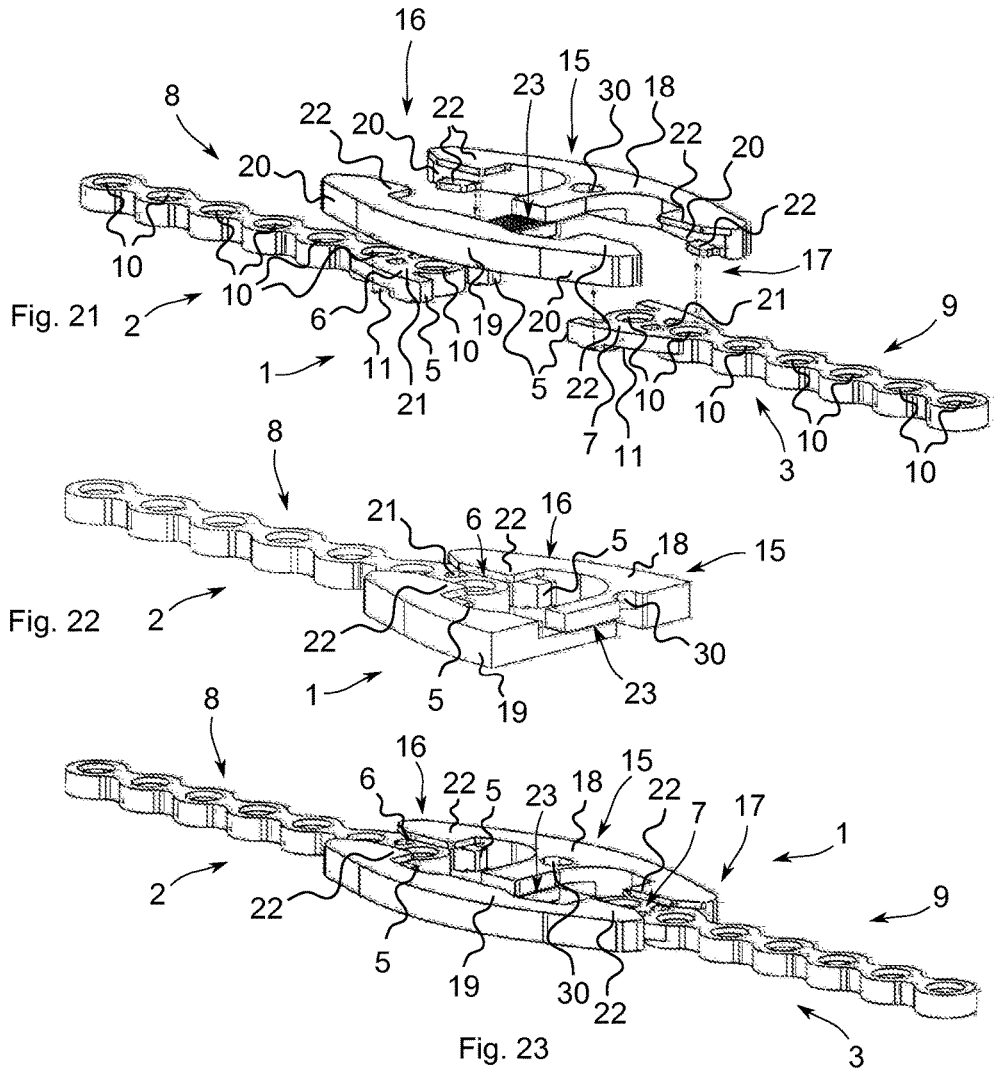
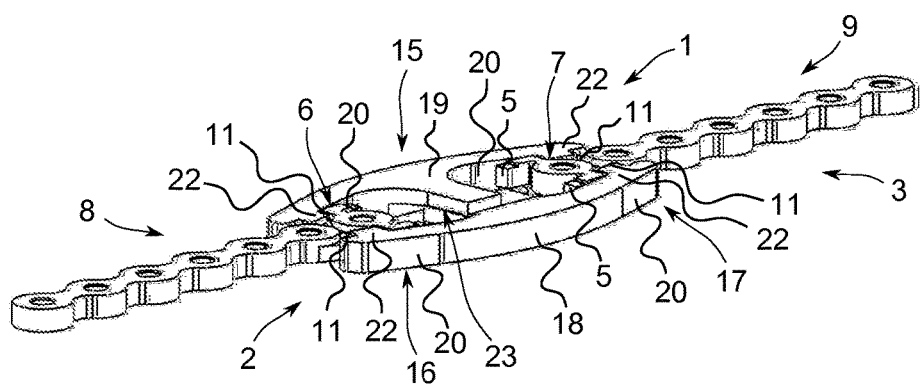
Fig. 24

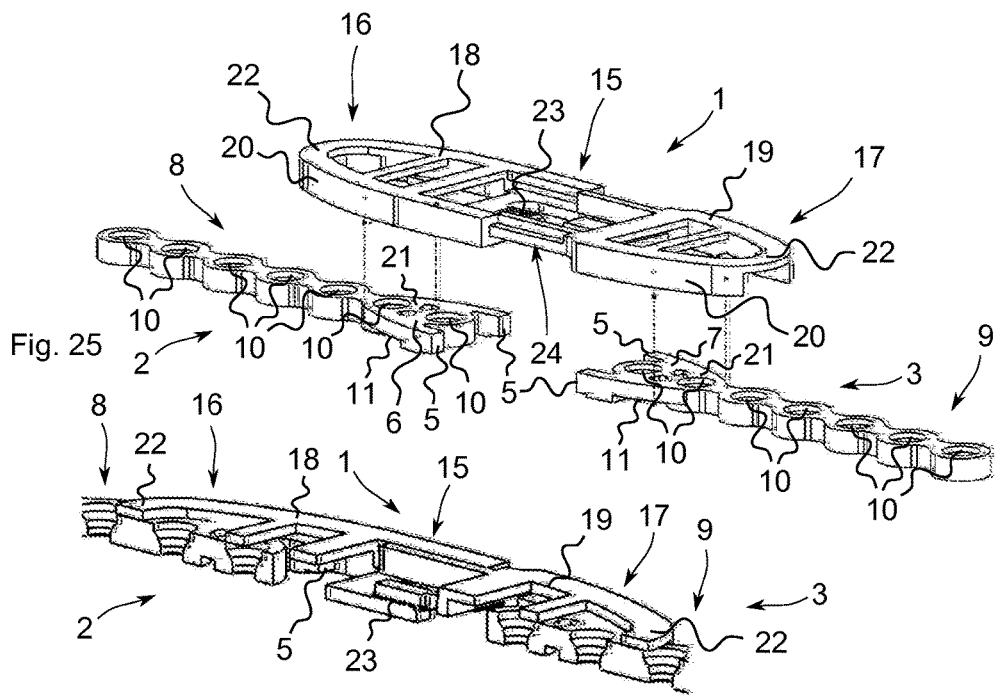
Fig. 25
Fig. 26
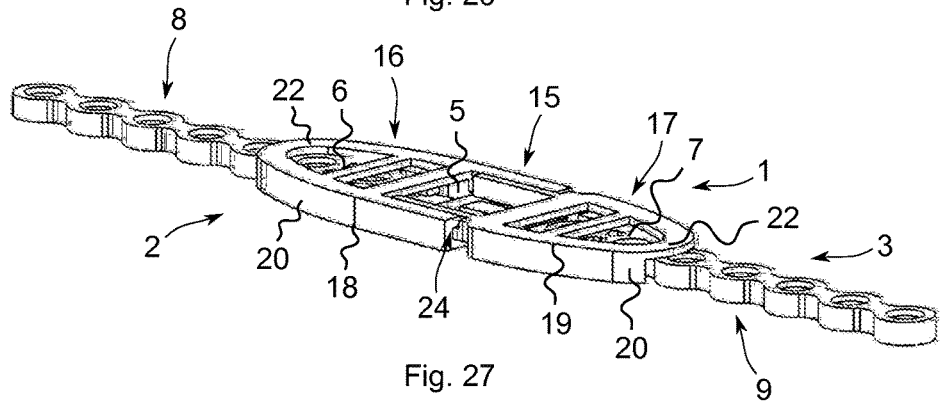
Fig. 27
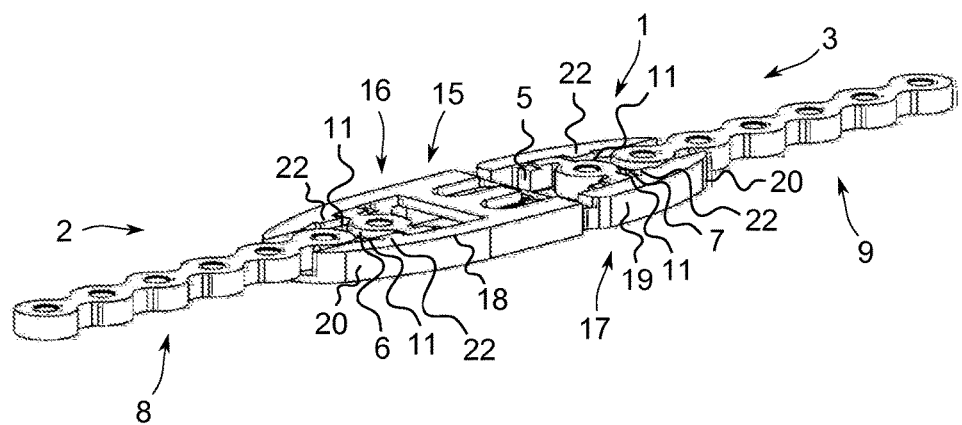
Fig. 28

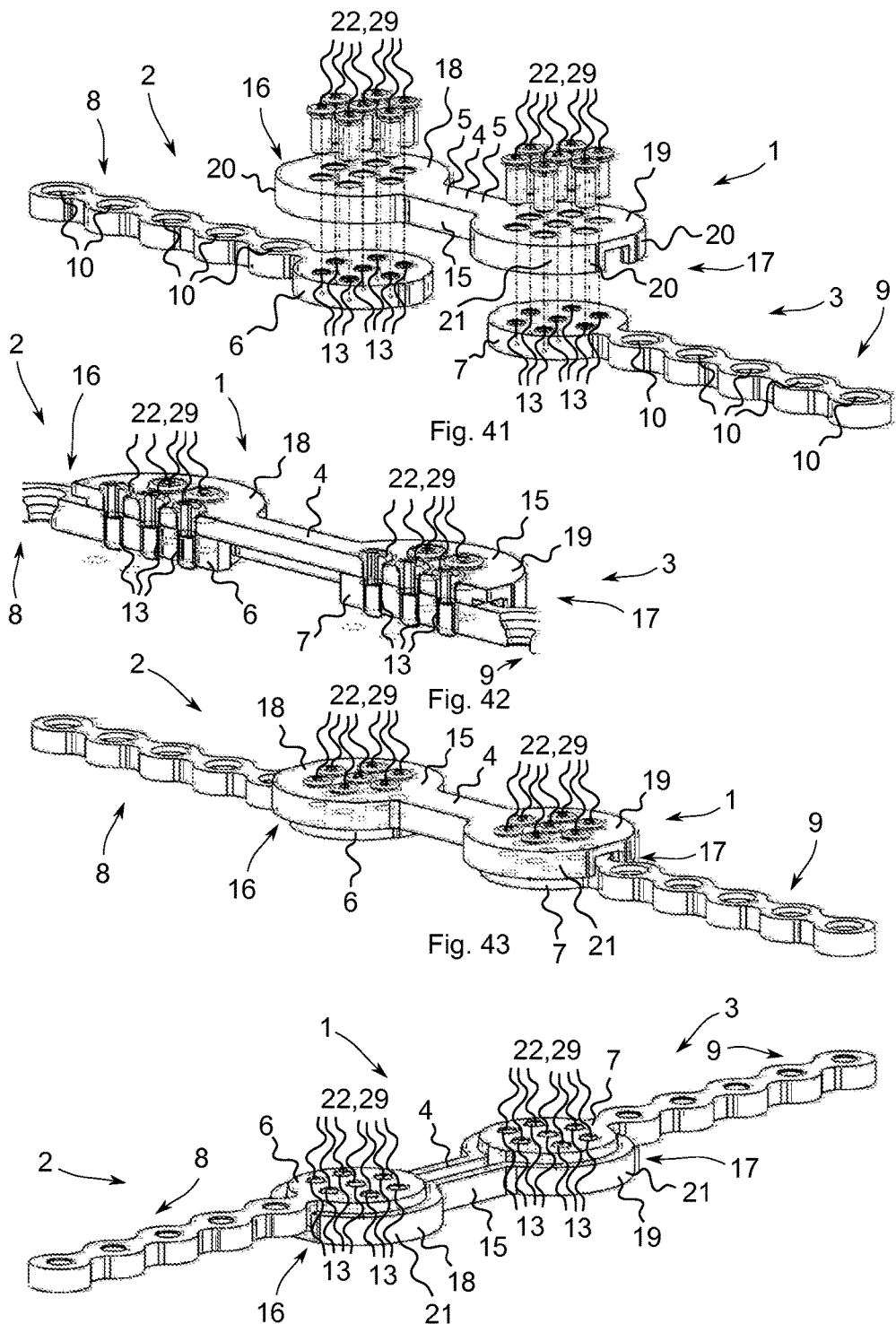

CLOSING MEMBER FOR STERNAL CLOSURE, STERNAL CLOSURE SYSTEM COMPRISING SUCH CLOSING MEMBER AND STERNAL CLOSURE

The invention relates to a closing member for a sternal closure which is adapted to be attached to a human or animal body in the area of the sternum for closing a cleft therein as well as a sternal closure system, comprising two spaced-apart first and second securing portions adapted to be mounted on the human or animal body on both sides of a cleft in the area of a sternum as well as such closing member. Furthermore, the invention relates to a sternal closure for bridging a cleft in a human or animal sternum, comprising a first securing portion for mounting on the one side of the cleft and a second securing portion for mounting on the other side of the cleft, as well as comprising a removing part bridging the cleft from the first securing portion to the second securing portion and being materially connected thereto, wherein the removing part is separable at two spaced-apart predetermined breaking points.

Conventional closing members, sternal closures and sternal closure systems comprising these components are known already from the state of the art. For example, plural differently designed sternal closures are known from US 2002/0128654 A1, wherein concretely a device for a bone joint above a fracture or osteotomy is disclosed. This device comprises a plate having an upper surface and a lower surface and comprising at least two bone fixing areas and a bridge area between the bone fixing areas, wherein each bone fixing area includes at least one opening and the bridge area forms a cleft between the bridge area and the bone for permitting the intervention of an appropriate severing device onto the bridge area. Also a securing means is comprised which is adapted to be arranged through the openings and to engage with the plate and to secure the bone fixing areas to one or more portions of a bone. However, all of these closures have the drawback that if once separated, for example during an emergency operation, they cannot be easily joined again in the area of the joint. For repeated closing of the sternum either a new sternal closure then would have to be secured being offset relative to the former severed sternal closure additionally in the area of the sternum or, alternatively thereto, first the former sternal closure would have to be removed and only then the new sternal closure could be inserted instead of the former one. In this way, re-closing/closing of a sternum repeatedly severed during an emergency operation is substantially impeded.

Moreover WO 2008/073898 A2 discloses a sternal closure comprising a first plate including a bone fixing area, wherein the bone fixing area has at least one counter-sunk opening for receiving a securing means for securing the plate on one side of the sternum, and a locking area comprising at least one protruding orientation element, and comprising a second plate including a bone fixing area, wherein the bone fixing area has at least one counter-sunk opening for receiving a securing means for securing the plate on an opposite side of the sternum, and a locking area dimensioned so that it contacts at least part of the locking area of the first plate. Moreover, a rotating element is provided which interacts with the at least one orientation element on the first plate for holding the first and second plates together and thus securing the opposite sides of the sternum, wherein the first and second plates can be separated from the at least one orientation element by uncoupling the rotating member. Although it is possible by this re-closable sternal closure to quickly re-open the sternum closed before in the case of medical emergency, it has turned out to be a drawback, however, that due to the overlapping areas of the bone fixing areas above the severing cleft in the sternum obstructions may occur during the medical intervention. Since the bone fixing areas directly cover the cleft of the severed sternum, it is not possible in the case of an already somewhat healed up sternum to open the sternum with the help of a saw without destroying the closure. Also in the case of a sternum which has not yet healed up sufficiently tightly obstructions may occur. The sternal halves either have to be forced/spread apart so far that impairments of the body to be treated by the spreading force to be applied may occur, or alternatively the treating physician has to operate laterally around these bone fixing areas, whereby the operating process can be obstructed.

Thus it is the object of the present invention to enable re-closing of a sternal closure in which an impairment of the operation process is to be avoided.

This object is achieved according to the invention by the fact that the closing member includes a first rear engaging area and a second rear engaging area, wherein, on the one hand, the first rear engaging area is prepared (i.e. arranged, dimensioned and orientated) for positive securing to a first mounting area (also referred to as first bone plate area) of the sternal closure on the one side of the cleft and, on the other hand, the second rear engaging area is prepared (i.e. arranged, dimensioned and orientated) for positive securing to a second mounting area (also referred to as second bone plate area) of the sternal closure on the other side of the cleft.

In this way a sternum opened once again after an emergency operation and closed at least already once before can be re-closed in a simple manner, thereby the closure time during operation being substantially reduced. At the same time, by the two spaced-apart rear engaging areas a cleft in the sternum exposed before is bridged and the severed sternal closure halves are sufficiently tightly joined, wherein each rear engaging area holds one half of the sternal closure at the mounting area. Thus also after re-closing a sufficiently strong cohesion of the sternum is provided for the subsequent healing, wherein especially the bond between the bone, the sternum and the mounting areas/bone plate areas is reinforced.

Further advantageous embodiments are claimed in the subclaims and will hereinafter be explained in detail.

When the closing member is configured to be divided/multi-part/multi-piece, for example split, or in one piece, an even more stable joint between the separated sternal closure halves is possible. In a split configuration, e.g. a splitting in the longitudinal direction (splitting plane extends in the longitudinal direction) or a splitting in the transverse direction (splitting plane extends transversely/obliquely or substantially normal to the longitudinal direction) the rear engaging areas of the closing member can first be inserted around tapered areas of the mounting areas/bone plate areas and thus can be arranged first in an unbraced state relative to each other at the mounting areas of the sternal closure. Only after that, the mounting areas are fixedly clamped in the closing member in a form-fit manner by moving the individual parts of the closing member toward each other and are slightly tensioned relative to each other so that the sternal halves are adjacent to each other preferably cleft-free via the connection to the mounting areas and are braced relative to/forced against each other.

When the closing member is materially separated from the sternal closure, the closing member can be taken off/removed from the sternal closure during the surgical intervention in the body to be treated. A centerpiece formed by the closing member therefore can be easily removed. Thus the treatment is further facilitated.

In accordance with a further embodiment it is also advantageous when the first and/or the second rear engaging area is formed as penetrating element, for example as journal, screw, hook, bolt or mandrel, and/or is configured as rib, lug, projection or ridge and/or forms a guide surface. The guide surface preferably is cup-shaped at the respective first and second rear engaging areas. Thus an especially stable, form-fit bonding of the mounting areas can be realized at the closing member. The penetrating elements, such as the lugs, can be directly inserted in recesses in the respective mounting areas and can be guided in the same especially during insertion.

In this context, it is also of advantage when the penetrating element is an integral part of the closing member or is configured as materially separate component and/or the penetrating element is part of a snap-fit. Thus an even more direct and stable bonding of the closing member to the mounting areas is possible.

When the snap-fit is inserted, in addition to a form-fit at the same or a different position, the structure of the closing member can be further facilitated and/or the closure force can be further increased by the closing member, as the snap-fit entails a strong retaining force.

When the guide surface is moreover orientated transversely/obliquely to the longitudinal direction of the sternal closure and/or transversely/obliquely to the longitudinal direction of the cleft, the closing member can align itself and the form-fit can be active when the rear engaging areas are slightly braced against each other via the guide surfaces to the mounting areas.

It is further expedient when a part of the closing member formed as first closing member half and a part of the closing member formed as second closing member half are connectable or connected to each other. In this way, the handling is further facilitated during re-closing, as the closing member can be attached/put on the mounting areas in one go.

When a detachable connection is realized between the first closing member half and the second closing member half, for example in the form of latching or screwing, an especially rapid fixing of the closing member to the mounting areas is possible. Therefore the time of re-closing the sternum is further reduced.

It is also useful when the latching or the screwing is formed to act in the longitudinal direction or transversely, preferably perpendicularly, to the longitudinal direction. Thus a multi-part, for example two-part structure of the closing member can be configured especially efficiently, as these two parts can be arranged directly adjacent each other and can directly form part of the latching or screwing. The complexity of components is thus further reduced and the number of the required components is reduced.

Concerning the screwed joint, it is further advantageous when it is structured as spindle drive in which spindle drive a spindle rod portion provided with a right-hand thread as well as a spindle rod portion provided with a left-hand thread is contained. The first spindle rod can be connected in a rotationally fixed manner e.g. to the first rear engaging area and the second spindle rod can be connected in a rotationally fixed manner e.g. to the second rear engaging area. When these two rods are arranged coaxially relative to each other, one single threaded sleeve (having a female thread) can be arranged centrally between these two rods and engage in the thread of the rods. Twisting the threaded sleeve in one direction then causes the rear engaging areas to simultaneously move toward each other or drift apart. Thus a stable securing of the rear engaging areas to each other which is easy to operate is made available.

Furthermore also a sternal closure system is provided comprising two first and second securing portions spaced apart from each other and adapted to be arranged on the human or animal body on both sides of a cleft in the area of the sternum as well as a closing member according to any one of the afore-mentioned embodiments. In this way the entire sternal closure system can be efficiently manufactured and a re-closable structure can be made available right from the start, i.e. before the sternal closure system is first mounted on the sternum. Hence re-opening/re-closing can be realized already during the first operation. Therefore a multi-part structure is of advantage.

It is also advantageous when in a closing position of the closing member for a tight connection of the first and second securing portions the first rear engaging area of the closing member positively engages in a first mounting area tightly connected to the first securing portion and the second rear engaging area of the closing member positively engages in a second mounting area tightly connected to the second securing portion. Thus the structure of the sternal closure system is further facilitated.

Furthermore a sternal closure is provided for bridging a cleft in a human or animal sternum, comprising a first securing portion for mounting on the one side of the cleft and a second securing portion for mounting on the other side of the cleft, and comprising a removing part bridging the cleft from the first securing portion to the second securing portion and being materially connected thereto, wherein the removing part is separable at two severing sites spaced apart from each other, wherein the removing part to be removable from the two securing portions is dimensioned so that a working orifice sufficiently large for a use of tools on the sternum can be reached between the first securing portion and the second securing portion. Thus also a sternal closure can be particularly efficiently produced.

Also a method for closing a cleft in a human or animal sternum by a sternal closure is comprised here in which method the sternal closure according to the afore-mentioned design is attached (e.g. screwed) to a bone and/or cartilage tissue.

Furthermore a method of producing a working orifice for a sternal severance or a sternal opening on a human or animal sternum is comprised here, wherein a sternal closure disposed at a bone and/or cartilage tissue according to the afore-mentioned configuration is severed at both severing sites and simultaneously the removing part is removed from the securing portions.

Further also a method of re-closing a sternal closure is comprised, wherein a closing member according to at least one of the afore-mentioned configurations is positively connected both to the first securing portion and to the second securing portion. Preferably the closing member is connected to the respective securing portion via the respective mounting area.

Figures 5, 6, 7, 8:
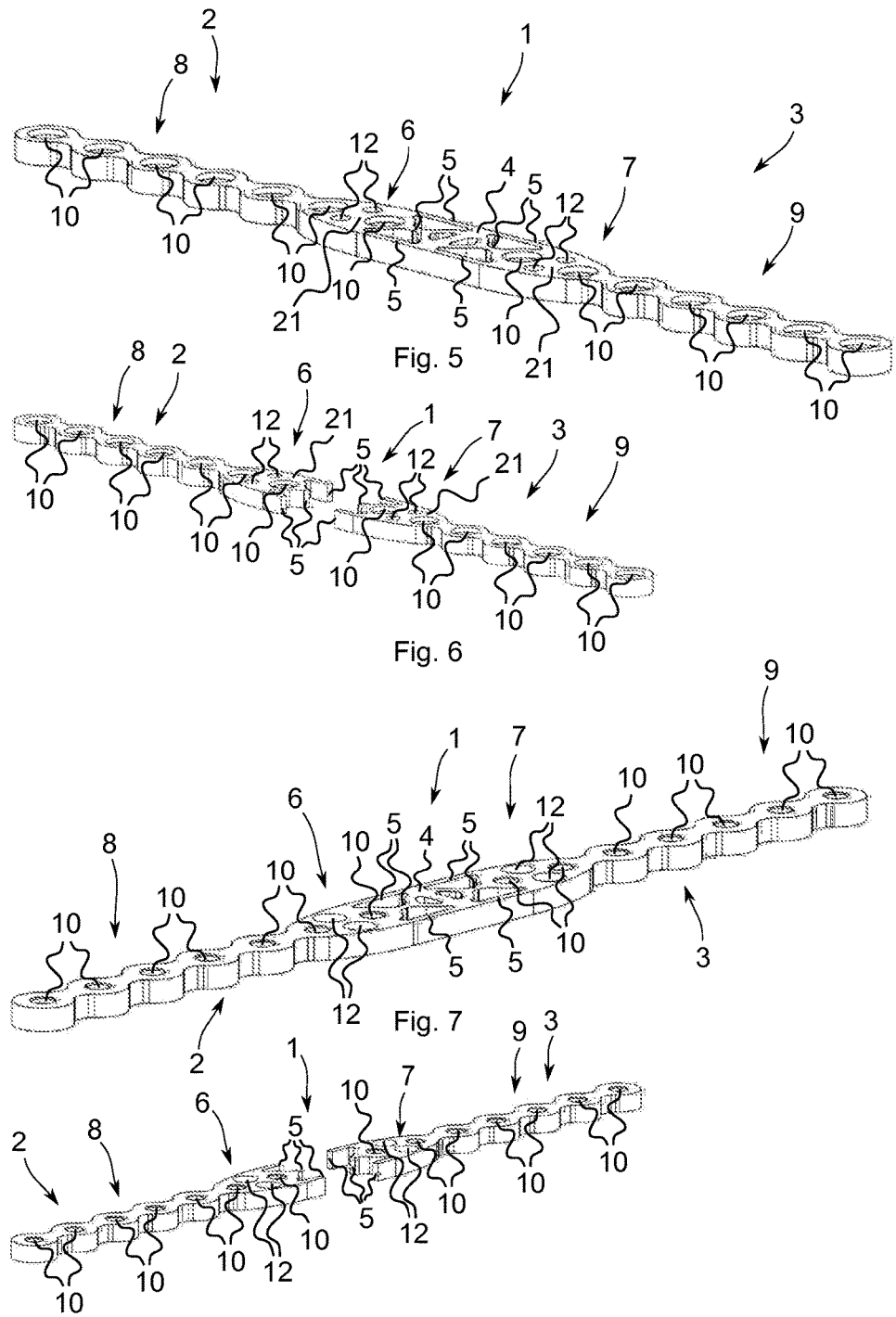
Figure 13:
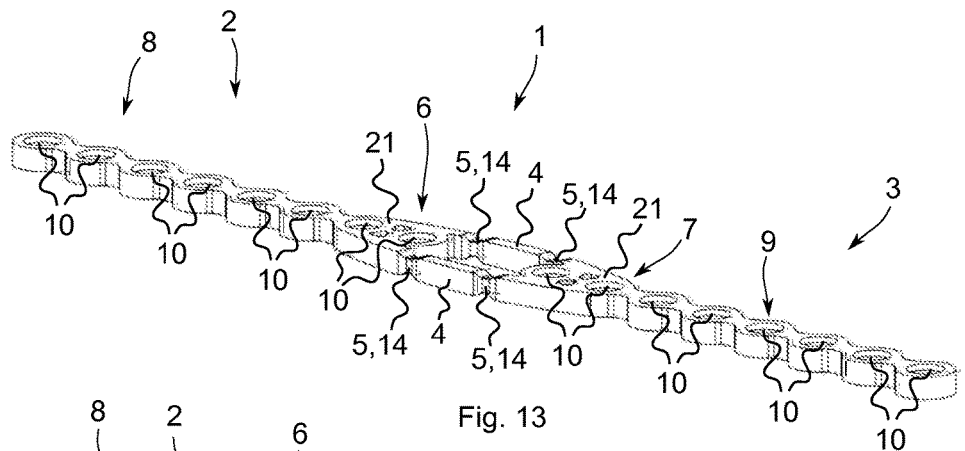
Figure 14:
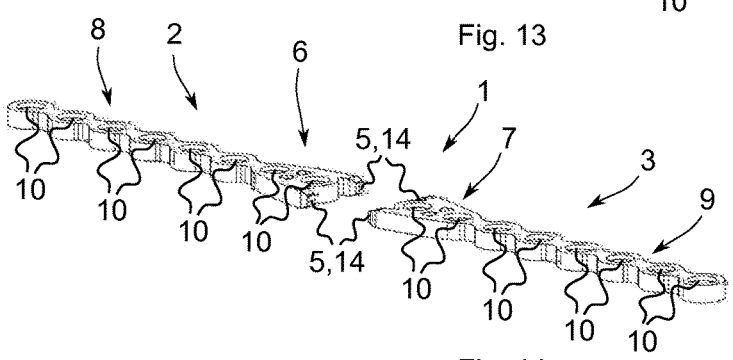
Figure 15:
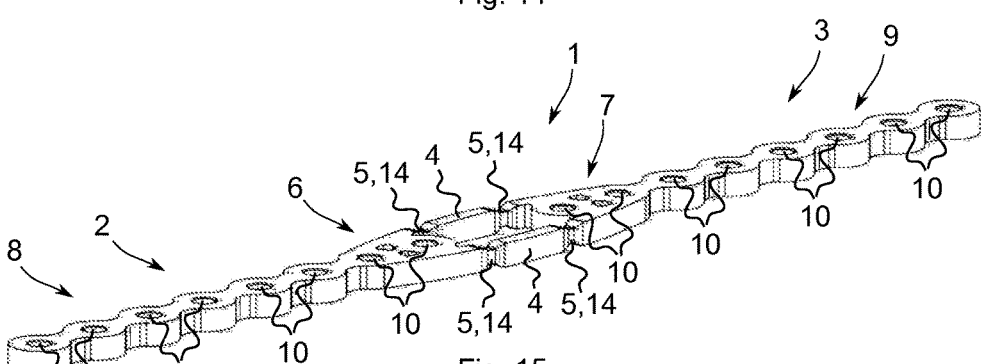
Figure 16:
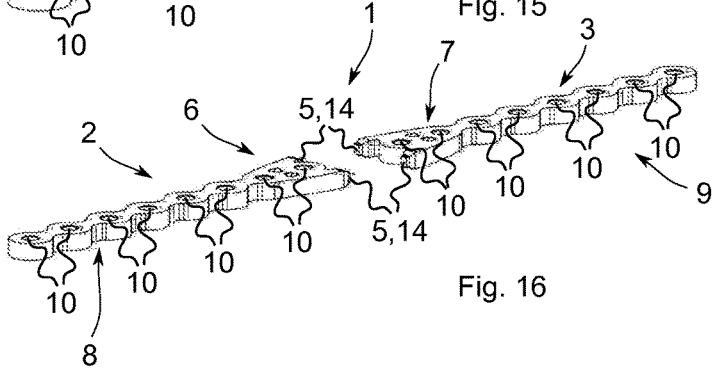
Figure 17:
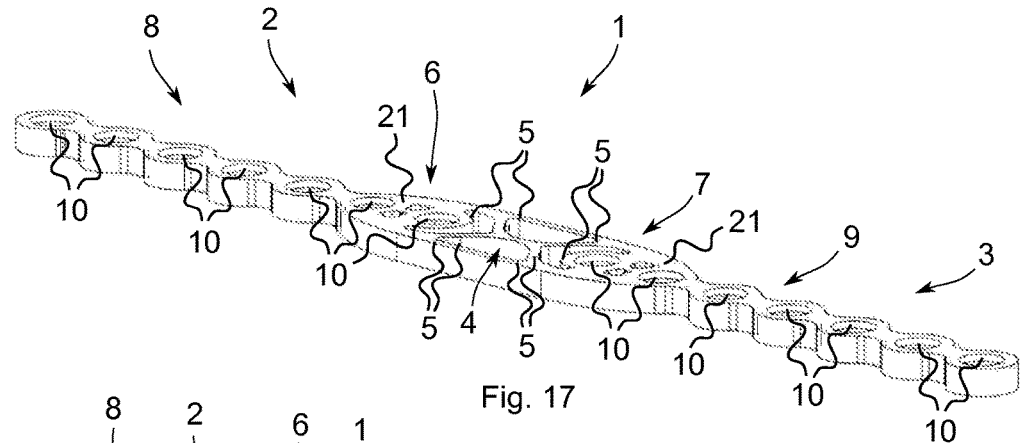
Figure 18:
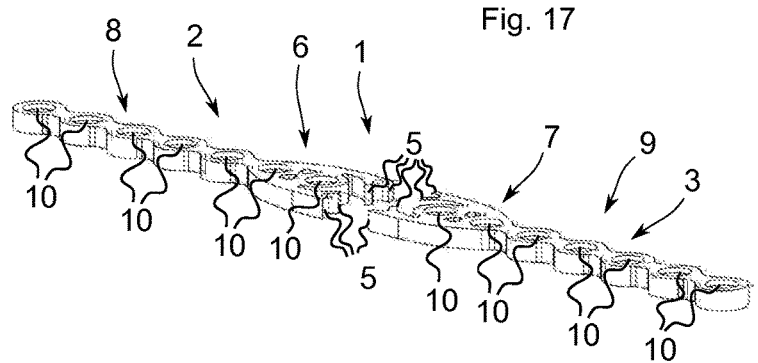
Figure 19:
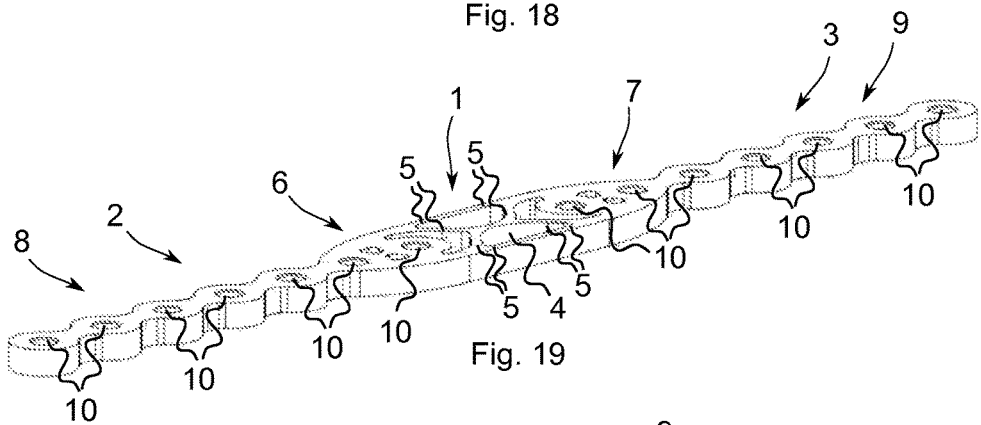
Figure 20:
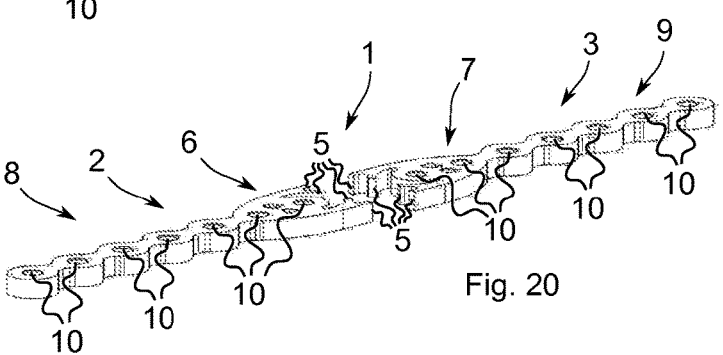
Figure 29:
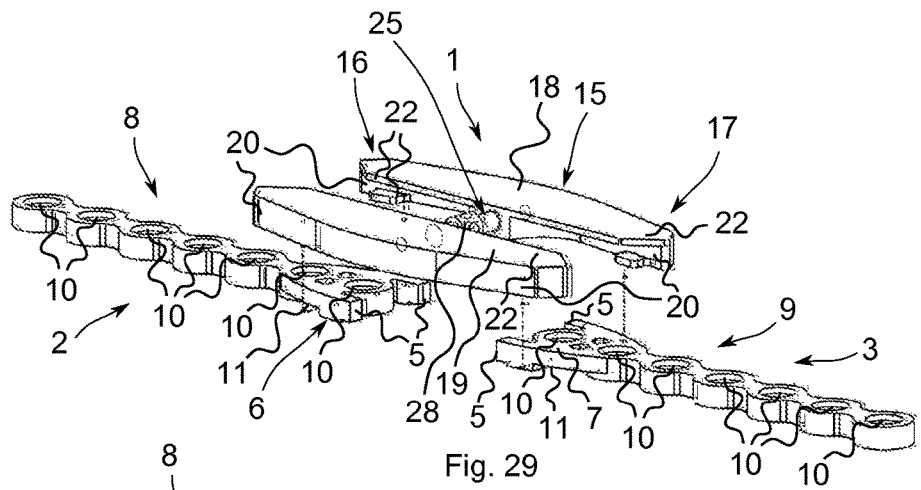
Figure 30:
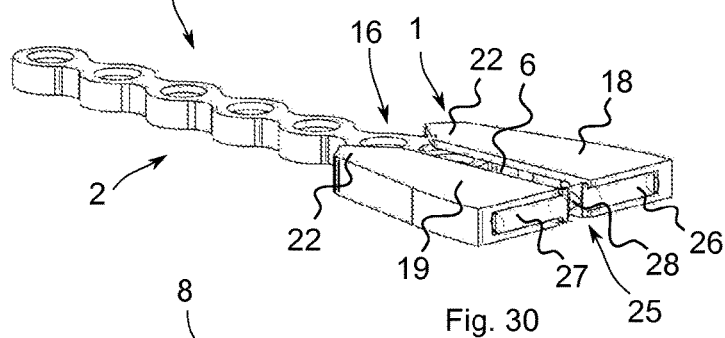
Figure 31:
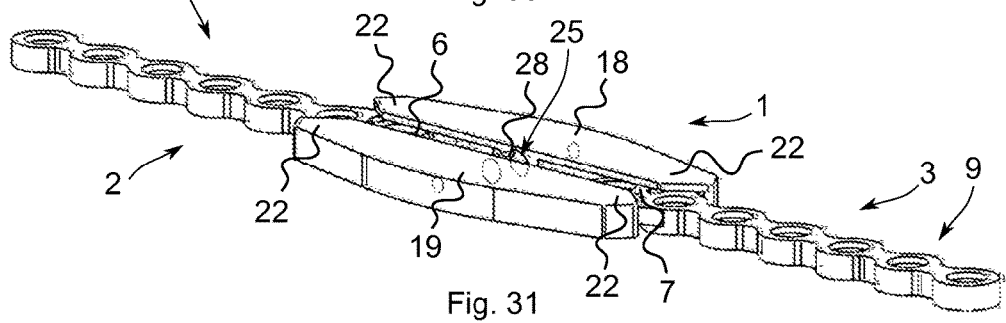
Figure 32:
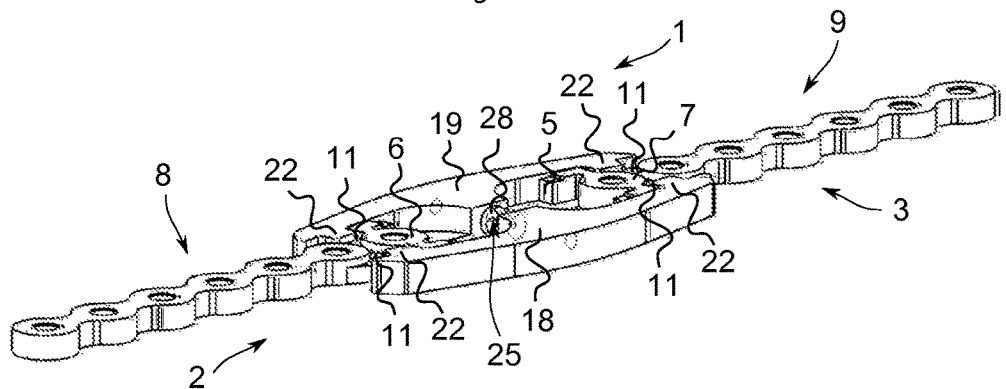
Figures 33, 34, 35, 36:
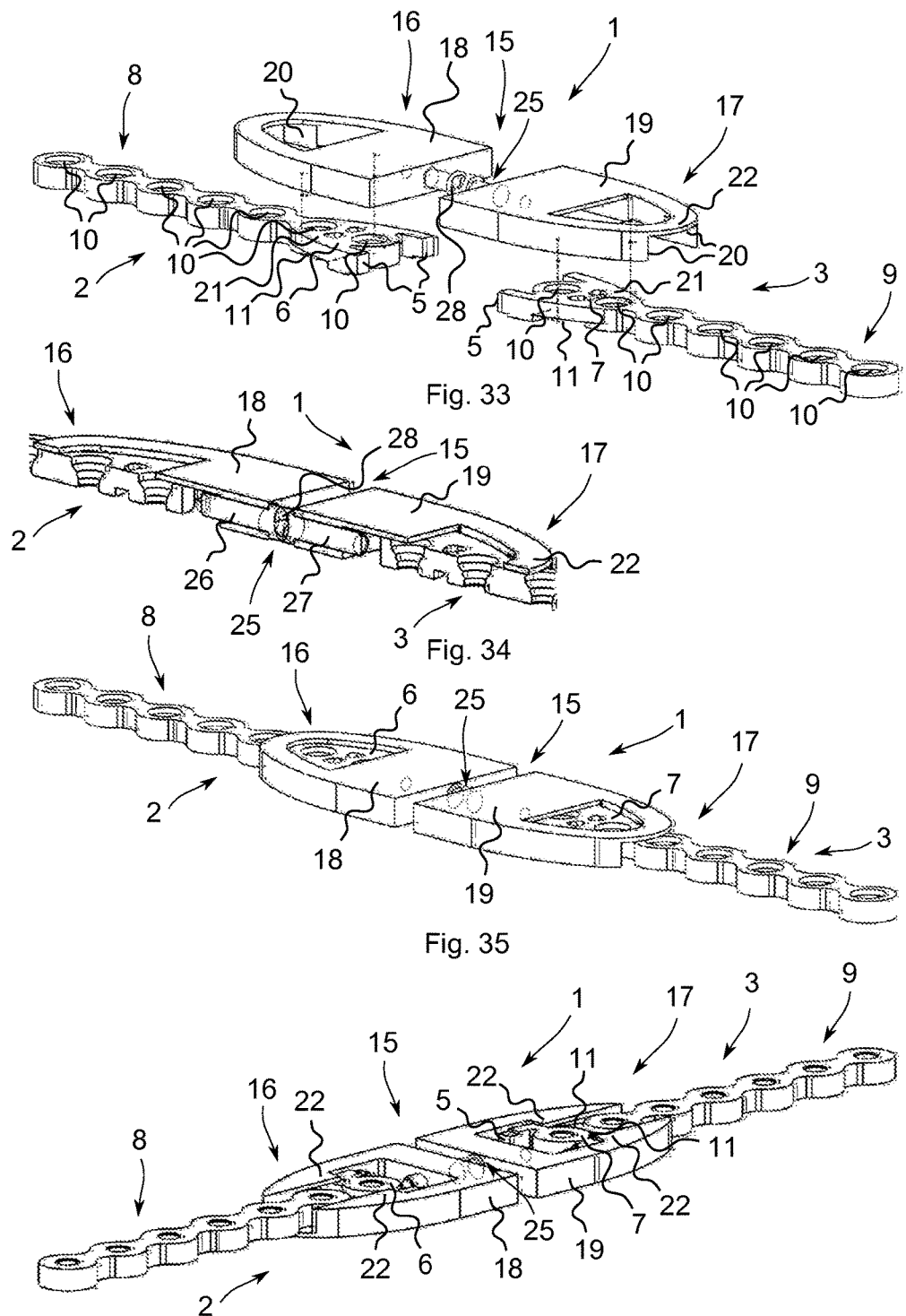
Figures 37, 38, 39, 40:
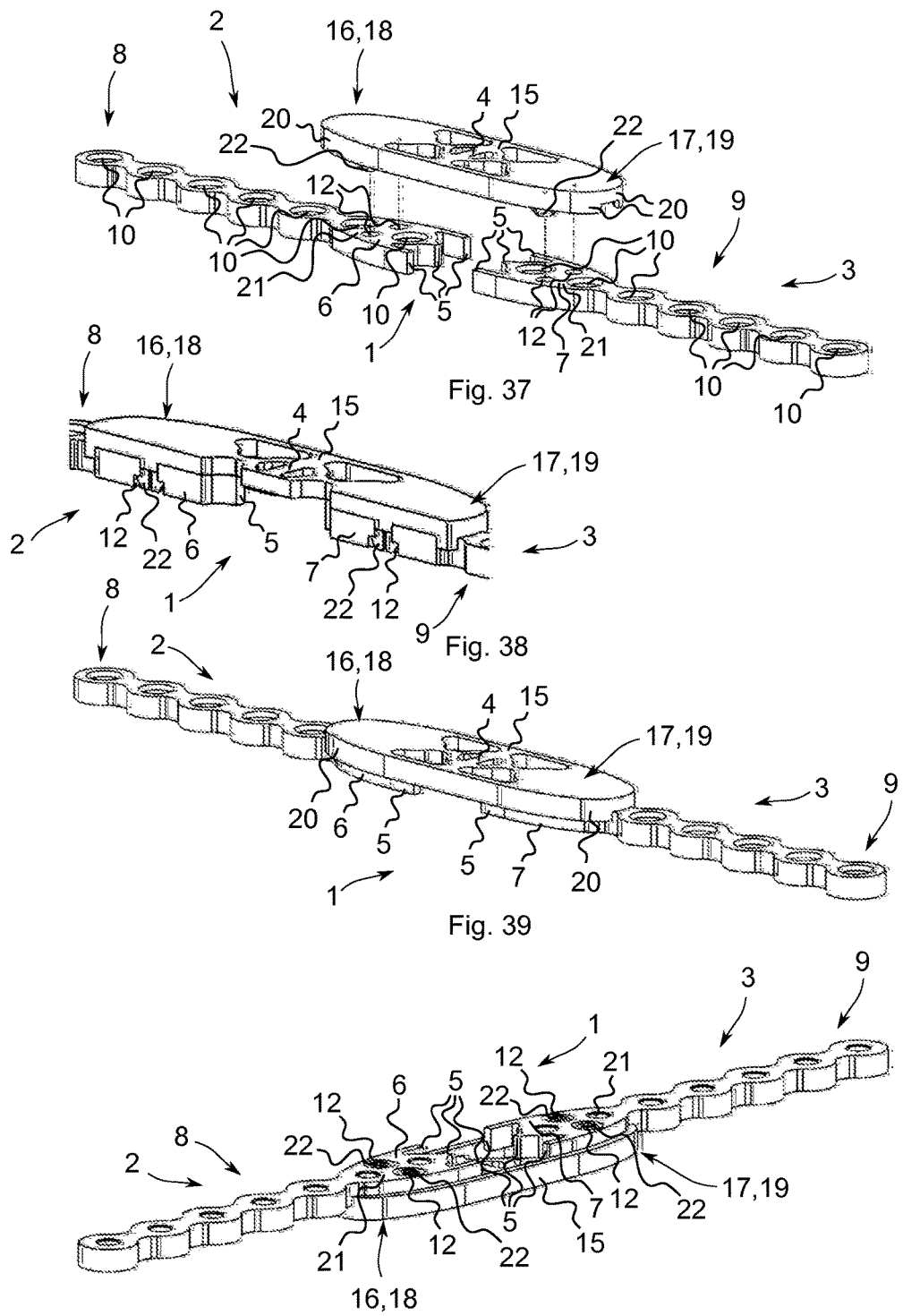

Hereinafter the invention is illustrated with the help of drawings in which different embodiments are shown, in which:

FIG. 1 shows an isometric representation of a sternal closure according to the invention in accordance with a first embodiment, wherein a front side of the sternal closure (i.e. a side facing the sternum in the secured state) is especially clearly evident and the two securing portions of the sternal closure are interconnected via a removing part, and wherein the sternal closure includes recesses into which a closing member can positively engage, FIG. 2 shows an isometric representation of the front side of the sternal closure illustrated in FIG. 1, wherein the sternal closure is provided in a condition in which the removing part is removed/withdrawn after severing at plural severing sites (two for each securing portion), FIG. 3 shows an isometric representation of the sternal closure shown in FIG. 1, wherein a rear side of the sternal closure (i.e. a side facing away from the sternum in the fastened state) is especially clearly evident and the sternal closure again is provided in the condition in which the removing part is connected to the securing portions, FIG. 4 shows an isometric representation of the rear side of the sternal closure already shown in FIG. 3, wherein the sternal closure is provided in a condition in which the removing part is removed/withdrawn after severing plural severing sites, FIG. 5 shows an isometric representation of a sternal closure according to the invention in accordance with a further embodiment, wherein a front side of the sternal closure (i.e. a side facing the sternum in the secured condition) is especially clearly evident and the two securing portions of the sternal closure are interconnected via a removing part, and wherein the sternal closure includes holes into which a snap element of a closing member can be positively inserted, FIG. 6 shows an isometric representation of the front side of the sternal closure shown in FIG. 5, wherein the sternal closure is provided in a condition in which the removing part is removed/withdrawn after severing at plural severing sites (three for each securing portion), FIG. 7 shows an isometric representation of the sternal closure shown in FIG. 5, wherein a rear side of the sternal closure (i.e. a side facing away from the sternum in the fastened condition) is especially clearly visible and the sternal closure again is provided in the condition in which the removing part is connected to the securing portions, FIG. 8 shows an isometric representation of the rear side of the sternal closure already illustrated in FIG. 7, wherein the sternal closure is provided in a condition in which the removing part is removed/withdrawn after severing at the severing sites, FIG. 9 shows an isometric representation of a sternal closure according to the invention in accordance with another embodiment, wherein a front side of the sternal closure (i.e. a side facing the sternum in the secured condition) is especially clearly evident and the two securing portions of the sternal closure are interconnected via a removing part, and wherein the sternal closure includes holes to which a securing means of a closing member is tightly connectable, FIG. 10 shows an isometric representation of the front side of the sternal closure shown in FIG. 9, wherein the sternal closure is provided in a condition in which the removing part is removed/withdrawn after severing at plural severing sites (one for each securing portion), FIG. 11 shows an isometric representation of the sternal closure illustrated in FIG. 9, wherein a rear side of the sternal closure (i.e. a side facing away from the sternum in the secured condition) is especially clearly visible and the sternal closure again is provided in the condition in which the removing part is connected to the securing portions, FIG. 12 shows an isometric representation of the rear side of the sternal closure already illustrated in FIG. 11, wherein the sternal closure is provided in a condition in which the removing part is removed/withdrawn after severing at the severing sites, FIG. 13 shows an isometric representation of a sternal closure according to the invention in accordance with a further embodiment, wherein a front side of the sternal closure (i.e. a side facing the sternum in the secured condition) is especially clearly evident and the two securing portions of the sternal closure are interconnected via a removing part, and wherein the sternal closure includes holes to which a securing means of a closing member is tightly connectable and the severing sites are visible by a tapered diameter of the removing part, FIG. 14 shows an isometric representation of the front side of the sternal closure shown in FIG. 13, wherein the sternal closure is provided in a condition in which the removing part is removed/withdrawn after severing at plural severing sites (two for each securing portion), FIG. 15 shows an isometric representation of the sternal closure illustrated in FIG. 13, wherein a rear side of the sternal closure (i.e. a side facing away from the sternum in the secured condition) is especially clearly evident and the sternal closure again is provided in the condition in which the removing part is connected to the securing portions, FIG. 16 shows an isometric representation of the rear side of the sternal closure already shown in FIG. 15, wherein the sternal closure is provided in a condition in which the removing part is removed/withdrawn after severing at the severing sites, FIG. 17 shows an isometric representation of a sternal closure according to the invention in accordance with a further embodiment, wherein a front side of the sternal closure (i.e. a side facing the sternum in the secured condition) is especially clearly evident and the two securing portions of the sternal closure are interconnected via a removing part, and wherein the sternal closure includes holes by which a securing means of a closing member is tightly connectable, FIG. 18 shows an isometric representation of the front side of the sternal closure illustrated in FIG. 17, wherein the sternal closure is provided in a condition in which the removing part is removed/withdrawn after severing at plural severing sites (four for each securing portion), FIG. 19 shows an isometric representation of the sternal closure illustrated in FIG. 17, wherein a rear side of the sternal closure (i.e. a side facing away from the sternum in the secured condition) is especially clearly evident and the sternal closure again is provided in the condition in which the removing part is connected to the securing portions, FIG. 20 shows an isometric representation of the rear side of the sternal closure already illustrated in FIG. 19, wherein the sternal closure is provided in a condition in which the removing part is removed/withdrawn after severing at the severing sites, FIG. 21 shows an isometric representation of a sternal closure-closing member-assembly in an exploded view, where the sternal closure according to FIGS. 1 to 4 is inserted and is provided in the condition in which the removing part is removed (FIGS. 2 and 4), and comprising a two-part closing member of a first embodiment which closing member is provided with projections adapted to be inserted in the recesses at mounting areas of the securing portions, FIG. 22 shows an isometric detailed view of one half of the sternal closure-closing member-assembly according to FIG. 21, wherein the closing member is shown in a condition arranged at one of the securing portions in which the projections are inserted in the recesses and the parts of the closing member are secured relative to each other by means of integrated latches, FIG. 23 shows an isometric representation of the entire sternal closure-closing member-assembly according to FIG. 21, wherein the closing member is provided in the condition shown in FIG. 22 and the front side of the sternal closure is shown, FIG. 24 shows an isometric representation of the rear side of the entire sternal closure-closing member-assembly according to FIGS. 22 and 23, FIG. 25 shows an isometric representation of a sternal closure-closing member-assembly according to the invention in an exploded view, in which the sternal closure according to FIGS. 1 to 4 is inserted and is provided in the condition in which the removing part is removed (FIGS. 2 and 4), and comprising a two-part closing member according to a further embodiment, wherein the parts of the closing member are arranged to be movable relative to each other in the longitudinal direction of the sternal closure, and wherein the closing member is provided with projections adapted to be inserted in the recesses at mounting areas of the securing portions, FIG. 26 shows an isometric detailed view of one half of the sternal closure-closing member-assembly according to FIG. 25, wherein the closing member is shown in a condition disposed in one of the securing portions in which the projections are inserted in the recesses and the parts of the closing member are secured relative to each other by means of integrated latches, FIG. 27 shows an isometric representation of the entire sternal closure-closing member-assembly according to FIG. 25, wherein the closing member is provided in the condition shown in FIG. 26 and the front side of the sternal closure is illustrated, FIG. 28 shows an isometric representation of the rear side of the entire sternal closure-closing member-assembly according to FIGS. 26 and 27, FIG. 29 shows an isometric representation of a sternal closure-closing member-assembly according to the invention in an exploded view, in which the sternal closure according to FIGS. 1 to 4 is inserted and is provided in the condition in which the removing part is removed (FIGS. 2 and 4), and comprising a two-part closing member according to another embodiment, wherein the parts of the closing member are arranged to be movable relative to each other in the transverse direction of the sternal closure, and wherein the closing member is provided with projections adapted to be inserted in the recesses at mounting areas of the securing portions, FIG. 30 shows an isometric detailed view of one half of the sternal closure-closing member-assembly according to FIG. 29, wherein the closing member is illustrated in a condition arranged on one of the securing portions in which the projections are inserted in the recesses and the parts of the closing member are secured relative to each other by means of a spindle drive, FIG. 31 shows an isometric representation of the entire sternal closure-closing member-assembly according to FIG. 29, wherein the closing member is provided in the condition shown in FIG. 30 and the front side of the sternal closure is illustrated, FIG. 32 shows an isometric representation of the rear side of the entire sternal closure-closing member-assembly according to FIGS. 30 and 31, FIG. 33 shows an isometric representation of a sternal closure-closing member-assembly according to the invention in an exploded view in which the sternal closure according to FIGS. 1 to 4 is inserted and is provided in the condition in which the removing part is removed (FIGS. 2 and 4), and comprising a two-part closing member according to a further embodiment, wherein the parts of the closing member are arranged to be movable relative to each other in the longitudinal direction of the sternal closure, and wherein the closing member is provided with projections adapted to be inserted in the recesses at mounting areas of the securing portions, FIG. 34 shows an isometric detailed view of one half of the sternal closure-closing member-assembly according to FIG. 33, wherein the closing member is shown in a condition disposed at one of the securing portions in which the projections are inserted in the recesses and the parts of the closing member are secured relative to each other by means of an integrated spindle drive, FIG. 35 shows an isometric representation of the entire sternal closure-closing member-assembly according to FIG. 33, wherein the closing member is provided in the condition shown in FIG. 34, and the front side of the sternal closure is illustrated, FIG. 36 shows an isometric representation of the rear side of the entire sternal closure-closing member-assembly according to FIGS. 34 and 35, FIG. 37 shows an isometric representation of a sternal closure-closing member-assembly according to the invention in an exploded view, in which the sternal closure according to FIGS. 5 to 8 is inserted and is provided in the condition in which the removing part is removed (FIGS. 6 and 8), and comprising a one-part closing member according to another embodiment, wherein the closing member is provided with a snap device adapted to engage in holes at mounting areas of the securing portions, FIG. 38 shows an isometric detailed view of one half of the sternal closure-closing member-assembly according to FIG. 37, wherein the closing member is shown in a condition disposed at one of the securing portions in which the snap device is engaged in the holes of the securing portions, FIG. 39 shows an isometric representation of the entire sternal closure-closing member-assembly according to FIG. 37, wherein the closing member is provided in the condition shown in FIG. 38 and the front side of the sternal closure is illustrated, FIG. 40 shows an isometric representation of the rear side of the entire sternal closure-closing member-assembly according to FIGS. 38 and 39, FIG. 41 shows an isometric representation of a sternal closure-closing member-assembly according to the invention in an exploded view, in which the sternal closure according to FIGS. 9 to 12 is inserted and is provided in the condition in which the removing part is removed (FIGS. 10 and 12), and comprising a one-part closing member according to another embodiment, wherein the closing member is provided with securing means adapted to be secured in holes at mounting areas of the securing portions, FIG. 42 shows an isometric detailed view of one half of the sternal closure-closing member-assembly according to FIG. 41, wherein the closing member is shown in a condition disposed at one of the securing portions in which the securing means are secured in the holes of the securing portions, FIG. 43 shows an isometric representation of the entire sternal closure-closing member-assembly according to FIG. 41, wherein the closing member is provided in the condition shown in FIG. 42 and the front side of the sternal closure is illustrated, and FIG. 44 shows an isometric representation of the rear side of the entire sternal closure-closing member-assembly according to FIGS. 42 and 43.

The Figures are merely schematic and only serve for the purpose of comprehension of the invention. Equal elements are provided with equal reference numerals.

In the FIGS. 1 to 20 different embodiments of a sternal closure 1 according to the invention are shown. Each of these sternal closures 1 serves for bridging a cleft in a human or animal sternum, especially for bridging a cleft extending in the longitudinal direction of the breastbone/sternum. The sternal closure 1 comprises a first securing portion 2 for mounting at a bone and/or cartilage tissue portion on the one side of the cleft and a second securing portion 3 for mounting on the other side of the cleft. Apart from these securing portions 2 and 3, the sternal closure 1 includes a removing part 4 bridging the cleft from the first securing portion 2 to the second securing portion 3 in the secured condition/operating condition of the sternal closure 1 and being materially connected thereto, wherein the removing part 4 is connected to each of the securing portions 2 and 3 on at least two severing sites 5 spaced apart from each other and is adapted to be severed at these sites. The removing part 4 thus adapted to be removed from both securing portions 2 and 3 is dimensioned so that a working orifice sufficiently large for the use of a tool at the sternum provided between the first securing portion 2 and the second securing portion 3 can be reached. The sternal closure 1 has an elongate, flat and thus plate-shaped extension.

As is clearly evident in FIG. 1, for example, the first securing portion 2 includes on the side facing the second securing portion 3 a thickened area which increases substantially transversely to the longitudinal direction and, as will be illustrated hereinafter, is provided for receiving a closing member 15. The thickened area of the first securing portion 2 is hereinafter referred to as first mounting area 6. Also the second securing portion 3 includes on the side facing the first securing portion 2 a thickened area which substantially increases transversely to the longitudinal direction and, as will be illustrated hereinafter, is provided for receiving a closing member 15. The thickened area of the second securing portion 3 is hereinafter referred to as second mounting area 7.

On the side of the first mounting area 6 facing away from the second securing portion 3 a ribbon-shaped basic portion 8, hereinafter referred to as first basic portion 8, is integrally connected. This first basic portion 8 is substantially configured as punched ribbon, wherein plural individual through-holes 10 (through-bores or through-cuttings, for example) are arranged along the longitudinal direction adjacent each other. Also on the side of the second mounting area 6 facing away from the first securing portion 2 a ribbon-shaped basic portion 9, hereinafter referred to as second basic portion 9, is integrally connected which is structured just as the first basic portion 8 and therefore is equally configured substantially as punched ribbon and includes plural individual through-holes 10 (through-bores or through-cuttings, for example) arranged along the longitudinal direction adjacent each other.

Each of the two mounting areas 6 and 7, too, includes at least one through-hole 10 (in the form of a through-bore). Each of the through-holes 10 is provided for interacting with a bone screw for mounting on a bone and/or a cartilage tissue of an animal or a human being, wherein the threaded portion of each of these screws can be put through one of the through-holes 10 and the screw head adjacent to this threaded portion in the mounted state of the bone screw forces the respective securing portion 2, 3 against the sternum. As an alternative to this mounting via screwed joint, also a locking closure between the screw head and the respective first or second securing portion 2, 3 would be possible.

As can be further taken from FIG. 1 in connection with FIG. 2, the sternal closure 1 illustrated in the embodiment according to FIGS. 1 to 4 includes four severing sites 5 (two severing sites 5 for each securing portion 2, 3). Those portions of the first and second securing portions 2, 3 including the severing sites 5 are land-shaped, which is why the removing part 4 is connected to the respective mounting area 6, 7 via two respective lands.

The sternal closure 1 is in the form of an integral component part which is held together materially (i.e. by material connection). This integral sternal closure 1 is suited for the first mounting on a sternum severed for the first time (i.e. for a first closure of the sternum). Also, the first securing portion 2 is configured to be substantially equal/mirror-inverted/symmetrical to the second securing portion 3.

When the sternum has to be re-opened after mounting the sternal closure 1 on the sternum by means of the bone screws, for example in the case of occurring emergency, the sternal closure 1 can be quickly re-opened. In such situation the severing sites 5 serve for quick severance of the sternal closure 1 and separation of the securing portions 2, 3 from each other. In FIG. 2 the sternal closure 1 is shown after severing the severing sites 5 and subsequent removal of the removing part 4. For example, the removing part 4 has been cut out or punched out.

Furthermore, it is evident in FIGS. 3 and 4 that on the rear side/lower side of the sternal closure 1 facing the sternum in the operating condition recesses 11 whose structure and functioning will be illustrated later in combination with FIGS. 21 to 36 are provided on each of the mounting areas 6, 7.

The second embodiment of the sternal closure 1 according to the invention is illustrated in FIGS. 5 to 8. In this second embodiment the first and second securing portions 2, 3 are configured substantially as the first and second securing portions 2, 3 of the configuration of FIGS. 1 to 4; therefore the basic structure thereof is applicable to this embodiment, too.

In contrast to the sternal closure 1 of the first embodiment (FIGS. 1 to 4), the sternal closure 1 according to FIGS. 5 to 8 primarily differs by the configuration of the removing part 4, especially at the connecting area of the removing part 4 including the first and second mounting areas 6, 7, i.e. in the area of the severing sites 5. The removing part 4 forms sort of a framework structure by which it is connected, on the one hand, to the first securing portion 2 and, on the other hand, to the second securing portion 3. The removing part 4 is connected to the first and second mounting areas 6, 7 via plural small lands, e.g. three lands for each securing portion 2, 3, instead of via two respective lands. Therefore also a total of at least six smaller severing sites 5 at which the removing part 4 can be separated by means of a separating tool are present between the mounting areas 6, 7 and the removing part 4. Moreover, the sternal closure 1 according to FIGS. 5 to 8 has no recesses 11 in the region of the first and second mounting areas 6, 7, but has a constant thickness in its longitudinal direction/over its length (thickness=extension normal to the longitudinal and transverse direction; transverse direction corresponds to the direction along the longitudinal direction of the breastbone/sternum).

Snap closure seats 12 introduced in the first and second mounting areas 6, 7 serve for accommodating a closing member 15, the more detailed structure and functioning of said seats will be explained hereinafter in combination with FIGS. 37 to 40.

Another (third) embodiment of the sternal closure 1 according to the invention is illustrated in FIGS. 9 to 12. In this embodiment the first and second securing portions 2, 3 are configured substantially like the first and second securing portions 2, 3 of the configuration as set forth in FIGS. 1 to 4; therefore the basic structure thereof is also applicable to this embodiment.

In contrast to the sternal closure 1 of the first embodiment (FIGS. 1 to 4), the sternal closure 1 according to FIGS. 9 to 12 in turn differs primarily by the configuration of the removing part 4, especially at the connecting area of the removing part 4 including the first and second mounting areas 6, 7, i.e. in the region of the severing sites 5. The removing part 4 is now connected to the first and second mounting areas 6, 7/the first and second securing portions 2, 3 via one land only instead of via two respective lands. Hence now only a total of two severing sites 5 are present between the mounting areas 6, 7 and the removing part 4. Also the sternal closure 1 according to FIGS. 9 to 12 has no recesses 11 in the region of the first and second mounting areas 6, 7 but has a constant thickness equally in the longitudinal direction/over its length.

However, also the first and second mounting areas 6, 7 are again configured for receiving a closing member 15. Each of the mounting areas 6, 7 has a substantially circular and/or plate-like shape. Plural respective securing means seats 13 serving for accommodating a closing member 15, as explained in detail hereinafter in connection with FIGS. 41 to 44, are introduced in the mounting areas 6, 7. The more detailed structure and the more detailed functioning of the securing means seats 13 therefore will be explained hereinafter in connection with FIGS. 41 to 44.

Another (fourth) embodiment of the sternal closure 1 according to the invention is illustrated in FIGS. 13 to 16. In this embodiment the first and second securing portions 2, 3 are designed substantially just as the first and second securing portions 2, 3 of the configuration according to FIGS. 5 to 8; therefore the basic structure thereof is also applicable to this embodiment.

In contrast to the sternal closure 1 of the embodiment of FIGS. 5 to 8, the sternal closure according to FIGS. 13 to 16 in turn differs primarily by the configuration of the removing part 4. Viewed in more detail, two rod-shaped removing parts 4 are juxtaposed, wherein each removing part 4 is connected at a severing site 5 to the first mounting area 6 and is connected at another severing site 5 to the second mounting area 7. Thus two lands are provided (two spaced removing parts 4) which interconnect the mounting areas 6, 7 at a total of four severing sites 5. Furthermore, the severing sites 5, as is evident especially clearly in the FIGS. 13 and 15, are geometrically visible by means of notches 14. Said notches 14 form sort of a predetermined breaking point in which forceps engage during opening of the sternal closure 1 so as to separate the two securing portions 2, 3 from each other with as little effort as possible.

Another (fifth) embodiment of the sternal closure 1 according to the invention is illustrated in FIGS. 17 to 20. In this embodiment the first and second securing portions 2, 3 are configured substantially like the first and second securing portions 2, 3 of the embodiment according to FIGS. 5 to 8; therefore the basic structure thereof is applicable to this embodiment, too.

In contrast to the sternal closure 1 of the embodiment of FIGS. 5 to 8, the sternal closure 1 according to FIGS. 17 to 20 in turn differs primarily by the configuration of the removing part 4, especially the configuration thereof in the region of the severing sites 5. The removing part 4 is now connected to the first and second mounting areas 6, 7 of the first and second securing portions 2, 3 via two split lands instead of via two respective lands. By means of these lands also this removing part 4 forms sort of a framework structure by which it is connected, on the one hand, to the first securing portion 2 and, on the other hand, to the second securing portion 3. Therefore, a total of eight severing sites 5 are present between the mounting areas 6, 7 and the removing part 4, at which sites the removing part 4 can be separated by means of a separating tool.

Hereinafter in FIGS. 21 to 44 various embodiments of a closing member 15 according to the invention are represented. The closing member 15 is always provided for being arranged on one of the sternal closures 1 according to FIGS. 1 to 20 and serves for repeated closing of the sternal closure 1 (which can be arranged at a human or animal body in the region of sternum for closing a cleft), after the removing part 4 has been removed before. In FIGS. 21 to 44 therefore the sternal closure 1 is always shown without a removing part 4. The closing member 15 further has a first rear engaging area 16 and a second rear engaging area 17, wherein, on the one hand, the first rear engaging area 16 is prepared/provided for positive securing to the first mounting area of the sternal closure 1 on the one side of the cleft and, on the other hand, the second rear engaging area 17 is prepared/provided for positive securing to the second mounting area 7 of the sternal closure 1 on the other side of the cleft. The closing member 15, as is clearly visible in FIG. 21, for example, is configured to be materially separated from the sternal closure 1. The closing member 15 can be configured to be divided/multi-part/multi-piece (FIGS. 21 to 36), for instance split, or in one piece (FIGS. 37 to 44).

In the FIGS. 21 to 24, to start with a first embodiment of a closing member 15 is shown. The closing member 15 shown here is split and includes a first closing member half 18 and a second closing member half 19. The two closing member halves 18, 19 according to FIGS. 21 to 24 are separated from each other along a partition plane extending in the longitudinal direction and are configured to be movable relative to each other in the respective transverse direction. Each of the first and second closing member halves 18, 19 are substantially designed as half-shells and extend in the longitudinal direction from the first mounting area 6 to the second mounting area 7. In a first end region (viewed in the longitudinal direction, i.e. the side of the closing member 15 facing the first securing portion 2 in the operating condition of the closing member 15) each of the two closing member halves 18, 19 forms a first rear engaging area 16. Also in a second end region opposed to the first end region (i.e. the second end region is the side of the closing member 15 facing the second securing portion 2 in the operating condition of the closing member 15) each of the two closing member halves 18, 19 forms a second rear engaging area 17. The two rear engaging areas 16, 17 are provided for securing to the afore-described sternal closures 1, especially the sternal closure 1 as set forth in FIGS. 1 to 4.

In the first rear engaging area 16 the first and second closing member halves 18, 19 include guide surfaces 20 extending transversely to the longitudinal direction and facing each other. In the first rear engaging area 16 a first guide surface 20 is arranged on the first closing member half 18 and a second guide surface 20 is arranged on the second closing member half 19. Each of the guide surfaces 20 extends in opposite direction/complementary to the outside of the first mounting area 6 facing the guide surface in a tapered area 21 (outside is the side interconnecting the front and rear sides). The outsides in the tapered area 21 extend transversely to the longitudinal direction such that the first mounting area 6 tapers in said tapered area 21 toward a side facing away from the second mounting area 7, as is also especially clearly visible in FIG. 21. The two guide surfaces 20 extend along the respective outside of the first mounting area 6. The two guide surfaces 20 of the first rear engaging area 16 therefore are provided for engaging behind the outside of the first mounting area 6.

A respective penetrating element 22 in the form of a lug (can also be referred to as rib, mandrel, projection, ridge or hook) is in turn connected to an upper side and a lower side of each guide surface 20. The penetrating elements 22 are an integral part of the closing member 15. The penetrating elements 22 extend along the respective front side and rear side and with their inner sides are preferably adjacent to the front side and the rear side of the first mounting area 6 in the operating condition. For positive interaction of the first mounting area 6 with the first rear engaging area 16 in the rear side of the first mounting area 6 furthermore recesses 11 (can also be referred to as groove or indentation) are provided for receiving the two penetrating elements 22 being adjacent thereto. Each of said recesses 11 provides a stop and guide surface in the longitudinal direction to which the respective penetrating element 22 is adjacent in the operating condition (as evident in FIGS. 22 to 24) and in turn engages behind the first mounting area 6. The first rear engaging area 16 therefore is formed by the guide surfaces 20 and the penetrating elements 22. The first mounting area 6 is thus connected tightly and positively to the first rear engaging area 16 in a mounted condition/an operating condition of the closing member 15.

The second rear engaging area 17 is structured just as the first rear engaging area 16, preferably configured symmetrically to the latter. Consequently, it also includes again a guide surface 20 for each closing member half 18, 19 as well as two penetrating elements 22 connected to each of said guide surfaces 20, such as lugs (can also be referred to as rib, mandrel, projection, ridge or hook). The rear side of the second mounting area 7, too, includes a recess 11 behind which the lugs engages and which thus positively connect the second mounting area 7 to the closing member 15 in interaction with the guide surfaces 20 at least in the operating condition. The second rear engaging area 17 is thus equally formed by the guide surfaces 20 and the penetrating elements 22.

The stop and guide surfaces of the recesses 11 are further arranged to extend obliquely relative both to the longitudinal direction and to the transverse direction of the sternal closure 1 offset thereto by 90° so that, when the closing member halves 18, 19 are pushed together in the transverse direction (as the penetrating elements 22 contact the stop and guide surfaces of the recesses 11), the securing portions 2 and 3 start moving toward each other. Upon closing the closing member 15 the guide surface 20 and the penetrating elements 22 of the closing member 15 encompass the securing portions 2 and 3 so that the securing portions 2 and 3 are moving toward each other. Hence the cleft in the sternum formed before is closed. The closure option thus closes a varying cleft width.

In other words, the two closing member halves 18, 19 are configured to be movable relative to each other transversely to the longitudinal direction and at the first and second end region (i.e. in the region of the first and second mounting area 6, 7) form sort of a forceps structure which is variable as to its spread and holds the respective mounting area 6, 7 via the guide surfaces 20. A latching 23 acting in the transverse direction serves for fixation in an inserted condition of the closing member 15 in the mounting areas 6, 7 (lugs and guide surfaces 20 engage behind the recess and the outside), wherein a first portion of the latching 23 including latching projections is materially connected to the first closing member half 18 and a second portion of the latching 23 including counter-latching projections is materially connected to the second closing member half 19. In the secured condition the latching projections and the counter-latching projections are interlocked and thus the two closing member halves 18, 19 are fixed by form-fit relative to each other.

Furthermore, on the closing member 15, i.e. on the first closing member half 18, as an alternative thereto also additionally, however, or instead on the second closing member half 19, a separating area 30 (cut point) may be provided on which the closing member 15 can be quickly re-opened in a repeated case of emergency. As is evident especially clearly in FIG. 21, the separating area 30 is applied to the first portion of the latching 23 including latching projections so that the respective portion can be separated from the further first closing member half 18 and then the two closing member halves 18, 19 can be pulled apart again and can be removed from the sternal closure 1.

Another embodiment of the closing member 15 is shown in FIGS. 25 to 26, wherein this embodiment is similar to the afore-described first embodiment according to FIGS. 21 to 24. However, this closing member 15 is not split longitudinally but transversely, i.e. along a plane which is normal to the longitudinal direction.

The first rear engaging area 16 consequently is formed by only one single closing member half, viz. the first closing member half 18. The second rear engaging area 16 is formed by the second closing member half 19. Each rear engaging area 16, 17 in turn is equipped with two guide surfaces 20 and with two penetrating elements 22 for each guide surface 20, the structure and extension thereof corresponding to the guide surfaces 20 and the penetrating elements 22 of the rear engaging areas 16, 17 of the design according to FIGS. 21 to 24. The rear engaging areas 16 and 17 in the operating condition interact with the first and second mounting areas 6 and 7 of the sternal closure 1 in the same way as those of the closing member 15 according to FIGS. 21 to 24.

Moreover, the two closing member halves 18, 19 are guided toward each other via a guide rail system/rail system 24 extending in the longitudinal direction. By means of a latching 23 the two closing member halves 18, 19 can in turn be braced with the mounting areas 6 and 7. The latching 23 does not act in the transverse direction but in the longitudinal direction. A first portion of the latching 23 including latching projections is materially connected to the first closing member half 18 and a second portion of the latching 23 including counter-latching projections is materially connected to the second closing member half 19. In the mounted condition the latching projections and the counter-latching projections are interlocked and thus the two closing member halves 18, 19 are positively fixed relative to each other.

In accordance with a further embodiment of the closing member 15, as it is shown in FIGS. 29 to 32, the latching 23 can also be replaced with a spindle drive 25. The remaining structure of the closing member 15 corresponds to the closing member design according to FIGS. 21 to 24. The spindle drive 25 which is visible especially clearly in FIG. 30 now serves as the element bracing the two closing member halves 18 and 19 in the operating condition with the mounting areas 6, 7. The spindle drive 25 includes a first spindle rod portion/a first spindle rod 26 which in turn has a first male thread screwed in (a female thread) of the first closing member half 18. Apart from the first spindle rod portion 26, the spindle drive 25 includes a second spindle rod portion/a second spindle rod 27 to which a second male thread is attached and which in turn is screwed in (a female thread) of the second closing member half 19. Both spindle rod portions 26, 27 (can also be referred to as threaded rod portions/threaded rods) are arranged on the closing member halves 18, 19 and positioned relative to each other so that they are orientated to extend coaxially with respect to each other. Moreover, the first male thread is configured in opposite direction to the second male thread. I.e. when the first male thread is a right-hand thread, the second male thread is a left-hand thread; or when the first male thread is a left-hand thread, the second male thread is a right-hand thread. At their end regions facing each other the two spindle rod portions 26, 27 are connected in a rotationally fixed manner, or are materially connected. In the connecting zone between the spindle rod portions 26, 27 the spindle drive 25 includes an operating portion 28 which is equally materially connected to the first and second spindle rod portions 26, 27. The operating portion 28 is provided for introducing an operating force driving the spindle drive 25 into the spindle rod portions 26 and 27. The operating portion 28 further has a tool holding structure, such as holes in the outer peripheral area, to which a tool can be positively attached so as to twist the operating portion 28 and thus the spindle rod portions 26, 27 (relative to the closing member halves 18, 19). When the operating portion 28 is twisted, due to the acceptance of the spindle rod portions 26, 27 in the closing member halves 18, 19 the closing member halves 18, 19 are displaced toward each other or apart from each other. As an alternative to the foregoing spindle drive design, the operating portion 28 can also be a separate component in the form of the threaded sleeve and can be materially separated from the two spindle rod portions 26, 27. Also the spindle rod portions 26, 27 then would be designed separately from each other/as separate components, wherein the first spindle rod portion 26 would no longer be accommodated to be twistable in the first closing member half 18 but would be held in a rotationally fixed manner, and also the second spindle rod portion 27 would no longer be accommodated to be twistable in the second closing member half 19 but would be held there in a rotationally fixed manner. The threaded sleeve then would be screwed onto the spindle rod portions 26, 27 at its end regions facing each other, the threaded sleeve for each spindle rod portion 26, 27 being provided with a female thread engaging in a male thread of the respective spindle rod portion 26, 27. Preferably the first and second male threads are different only regarding their direction of rotation and are designed equally regarding the diameter and the flank lead so that the threaded sleeve might have a constant inner diameter. The threaded sleeve interacts with the spindle rod portions 26 and 27 so that upon rotation of the threaded sleeve in a first direction of rotation again both spindle rod portions 26 and 27 and thus the two closing member halves 18 and 19 are moved toward each other, and upon rotation of the threaded sleeve 28 in a second direction of rotation opposed to the first direction of rotation both closing member halves 18 and 19 are moved apart from each other. Thus the distance between the closing member halves 18 and 19 can be adjusted in an especially simple manner.

FIGS. 33 to 36 illustrate another embodiment of the closing member 15 whose structure substantially corresponds to the structure of the closing member 15 according to FIGS. 25 to 28. The latching 23 in this case is replaced with the spindle drive 25. Merely the orientation of the spindle drive 25 has changed. Now the spindle drive 25 is orientated with its longitudinal direction in parallel to the longitudinal direction of the sternal closure 1 (in the operating condition) and no longer in the transverse direction. The anchoring of the spindle rod portions 26 and 27 on the respective closing member halves 18 and 19 and the remaining configuration of the spindle drive 25 corresponds to the already illustrated design according to FIGS. 29 to 32.

Another embodiment of the closing member 15 is shown in FIGS. 37 to 40, the structure thereof substantially corresponding to the structure of the closing member 15 according to FIGS. 21 to 24. The first and second closing member halves 18, 19 are integrally designed and materially interconnected, however. The first closing member half 18 is non-displaceable relative to the second closing member half 19. The closing member halves 18, 19 again have a half-shell shape but they can be secured in any other way to the first and second mounting areas 6, 7 of the sternal closure 1, especially of the sternal closure 1 according to FIGS. 5 to 8. The first rear engaging area 16 arranged at the first closing member half 18 includes two penetrating elements 22. Also the second rear engaging area 17 arranged at the second closing member half 19 includes two penetrating elements 22. Also the second rear engaging area 17 arranged at the second closing member half 19 includes two penetrating elements 22. Each of the penetrating elements 22 is in the form of a journal-shaped projection/journal and is materially connected to the closing member halves 18, 19. This journal has an annular projecting area adapted to be engaged in a snap fit seat 12 in the form of a hole/bore of the respective mounting area 6, 7 while a snap connection/a snap fit is formed. The journals are orientated to extend substantially perpendicularly to the sternum.

Another embodiment of the closing member 15 is shown in FIGS. 41 to 44, the structure thereof resembling that of the closing member 15 according to FIGS. 37 to 40. In this case, too, the first and second closing member halves 18, 19 are integrally formed in one piece and are materially interconnected. The closing member 15 is configured, however, to re-close the sternal closure 1 according to FIGS. 9 to 12 after removal of the removing part 4. Each of the closing member halves 18 and 19 therefore has a round shell shape in the inside of which the circular first or second mounting area 6, 7 is arranged while the outside and the front side/upper side of the first/second mounting area 6, 7 contacts the inside/inner surface of the first/second closing member half 18, 19.

Furthermore, the penetrating elements 22 are not configured as latching journals but as securing means 29, viz. a screw, alternatively a bolt or rivet, which are materially separated from the closing member halves 18, 19. Each securing means 29 interacts with a securing means seat 13 in the first or second mounting area 6, 7. For supporting a securing means 29, as is clearly evident from FIG. 42, the first and second closing member halves 18, 19 include a through-hole, preferably a through-bore, through which a securing portion (e.g. a threaded portion in a screw) is put/projects in the operating condition of the closing member 15 (i.e. the condition in which the closing member is tightly connected to the sternal closure 1 separated before). A head (e.g. a screw head of a screw) is tightly adjacent to the side facing away from the sternal closure 1/the front/upper side of the closing member 15, whereby the securing means 29 is supported toward one side. The securing means 29 is tightly held/fixed in the first or second mounting area 6, 7 in the securing means seat 13 (e.g. a female thread of a screw) by a region (e.g. of the threaded portion of the screw) projecting through the closing member 15/the respective closing member half 18, 19. Therefore these penetrating elements 22 again constitute the first and second rear engaging areas 16, 17. For each rear engaging area 16, 17 plural, preferably between two and ten, further preferably between five and eight, especially preferred seven securing means 29 are provided, each being associated with a through-hole and a securing means seat 13 and interacting with the same.

Even if it is not explained in more detail, the sternal closures 1 of the embodiments according to FIGS. 16 to 20 are provided for interacting with one of the closing members 15 and for being tightly connected by said closing member 15 when removing parts 4 are removed. Preferably, also these sternal closures 1 include at least seats for positively and/or non-positively supporting the penetrating elements 22 (e.g. the recesses 11, the snap-fit seats 12 or the securing means seats 13).

Furthermore, a sternal closure 1 (with or without a removing part 4) and a closing member 15 interacting with the same form a sternal closure system according to the invention, wherein, as already described, in a closing position of the closing member 15 for tight connection of the first to the second securing portions 2, 3, the first rear engaging area 16 of the closing member 15 positively engages in the first mounting area 6 tightly connected to the first securing portion 2, 3 and the second rear engaging area 17 of the closing member 15 positively engages in a second mounting area 7 tightly connected to the second securing portion 3.

As is further evident, especially in connection with FIGS. 37 to 44, each of the closing members 15 again also has a separating device of the type of a removing part 4 which interconnects the rear engaging areas 16, 17 and which removing part 4 is substantially structured and acts like the removing part 4 of the sternal closure 1. Therefore the closing member 15 can equally be severed by a severing tool, in the case of a repeatedly occurring emergency, without initially detaching the penetrating elements 22 from the mounting areas 6, 7.

For closing a cleft in a human or animal sternum by a sternal closure 1, one of the sternal closures 1 according to the foregoing design is disposed (e.g. screwed) on a bone and/or cartilage tissue. The sternal closure 1, as it is shown e.g. in FIG. 1, is placed with its rear side/lower side to bone or cartilage tissue tightly joined with the sternum, wherein the first securing portion 2 is placed on a first side (e.g. the left side) of the cleft and the second securing portion 3 is placed on a second side (e.g. the right side) of the cleft. The first mounting area 6 is directly secured to the sternum by means of bone screws (not shown for the sake of clarity) on the first side of the cleft. The first basic portion 8 then is equally secured, e.g. by means of further bone screws, on the first side, such as on the sternum or on ribs of the thorax. The second mounting area 7 is directly secured to the sternum by means of bone screws (not shown for the sake of clarity) on the second side of the cleft. The second basic portion 9 then is equally secured, by means of further bone screws, for example, on the second side, such as on the thorax/ribs or sternum of the thorax.

Furthermore, for producing a working orifice for a sternal severance or a sternal opening on a human or animal sternum, the sternal closure 1 according to any one of the afore-mentioned configurations disposed on a bone and/or cartilage tissue is severed at the severing sites 5 and at the same time the removing part 4 is removed from the securing portions 2, 3 (cf. e.g. FIG. 1 in connection with FIG. 2).

For re-closing the sternal closure 1 one of the closing members 15 according to at least one of the afore-mentioned configurations is positively connected both to the first securing portion 2 and to the second securing portion 3, as disclosed e.g. in connection with FIGS. 21 to 23. Preferably the closing member 15 is connected to the respective securing portion 2, 3 via the respective mounting area 6, 7.

Moreover, the closing member 15 and/or the sternal closure 1 is/are completely or partly made of metal, preferably a titanium material/a titanium alloy, especially preferred of a shape memory metal, or further preferred of a plastic material such as PEEK or PEKK.

The invention claimed is:

1. A closing member for a sternal closure adapted to be arranged on a human or animal body in the area of the sternum for closing a cleft therein, wherein the closing member includes a first rear engaging area and a second rear engaging area, wherein, on the one hand, the first rear engaging area is prepared for positive securing on a first mounting area of the sternal closure on the one side of the cleft and, on the other hand, the second rear engaging area is prepared for positive securing on a second mounting area of the sternal closure on the other side of the cleft, wherein a component of the closing member formed as a first closing member half is detachably connected with another component of the closing member formed as a second closing member half, and in a first end portion each of the first and second closing member halves is forming the first rear engaging area and in a second end portion that is arranged opposite to the first end portion each of the first and second closing member halves is forming the second rear engaging area, and wherein a latching forming the detachable connection is configured to act transversely to a longitudinal direction of the closing member, and wherein at least one of the first closing member half and the second closing member half is provided with a row of toothing of the latching, wherein the row of toothing is formed integrally with the first closing member half or the second closing member half, and wherein the row of toothing extends transversely to the longitudinal direction of the closing member.

2. The closing member according to claim 1 wherein the closing member is materially separated from the sternal closure.

3. The closing member according to claim 1, wherein at least one of the first and the second rear engaging area is in the form of a penetrating element.

4. The closing member according to claim 3, wherein the penetrating element is an integral part of the closing member or is a materially separate component.

5. The closing member according to claim 3, wherein the penetrating surface forms a guide surface and wherein the guide surface is orientated transversely to the longitudinal direction of the sternal closure and/or transversely to the longitudinal direction of the cleft.

6. The closing member according to claim 3, wherein the penetrating element includes a journal, screw, hook, bolt or mandrel, and/or forms a guide surface.

7. The closing member according to claim 3, wherein the penetrating element is part of a snap fit.

8. A closing member for a sternal closure adapted to be arranged on a human or animal body in the area of the sternum for closing a cleft therein, wherein the closing member includes a first rear engaging area and a second rear engaging area, wherein, on the one hand, the first rear engaging area is prepared for positive securing on a first mounting area of the sternal closure on the one side of the cleft and, on the other hand, the second rear engaging area is prepared for positive securing on a second mounting area of the sternal closure on the other side of the cleft, wherein a component of the closing member formed as a first closing member half is detachably connected with another component of the closing member formed as a second closing member half, and in a first end portion each of the first and second closing member halves is forming the first rear engaging area and in a second end portion that is arranged opposite to the first end portion each of the first and second closing member halves is forming the second rear engaging area, and wherein a latching forming the detachable connection is configured to act transversely to a longitudinal direction of the closing member, wherein at least one of the first and the second rear engaging area is in the form of a penetrating element, and wherein the penetrating element is part of a snap fit and the snap-fit is inserted, in addition to a form-fit at the same or a different position.

9. A sternal closure system comprising two first and second securing portions spaced apart from each other and adapted to be arranged on the human or animal body on both sides of a cleft in the area of a sternum as well as a closing member for a sternal closure adapted to be arranged on a human or animal body in the area of the sternum for closing a cleft therein, wherein the closing member includes a first rear engaging area and a second rear engaging area, wherein, on the one hand, the first rear engaging area is prepared for positive securing on a first mounting area of the sternal closure on the one side of the cleft and, on the other hand, the second rear engaging area is prepared for positive securing on a second mounting area of the sternal closure on the other side of the cleft, wherein a component of the closing member formed as a first closing member half is detachably connected with another component of the closing member formed as a second closing member half, and in a first end portion each of the first and second closing member halves is forming the first rear engaging area and in a second end portion that is arranged opposite to the first end portion each of the first and second closing member halves is forming the second rear engaging area, and wherein a latching forming the detachable connection is configured to act transversely to a longitudinal direction of the closing member.

10. The sternal closure system according to claim 9, wherein a closing position of the closing member for tight connection of the first and second securing portions the first rear engaging area of the closing member positively engages in a first mounting area tightly connected to the first securing portion and the second rear engaging area of the closing member positively engages in a second mounting area tightly connected to the second securing portion.

* * * * *